(12) United States Patent
Royalty

(10) Patent No.: US 8,241,197 B2
(45) Date of Patent: Aug. 14, 2012

(54) METHOD OF GENERATING A CARDIOGRAM WITH A MAGNET

(76) Inventor: John W Royalty, Crystal River, FL (US)

( * ) Notice: Subject to any disclaimer, the term of this patent is extended or adjusted under 35 U.S.C. 154(b) by 878 days.

(21) Appl. No.: 11/648,637

(22) Filed: Jan. 3, 2007

(65) Prior Publication Data

US 2007/0156055 A1 Jul. 5, 2007

Related U.S. Application Data

(60) Provisional application No. 60/755,413, filed on Dec. 31, 2005, provisional application No. 60/755,414, filed on Dec. 31, 2005, provisional application No. 60/755,415, filed on Dec. 31, 2005, provisional application No. 60/755,416, filed on Dec. 31, 2005, provisional application No. 60/755,424, filed on Dec. 31, 2005.

(51) Int. Cl.
*A61N 1/362* (2006.01)
*A61B 1/00* (2006.01)
(52) U.S. Cl. ......................................... 600/16; 600/129
(58) Field of Classification Search .................... 600/16, 600/129
See application file for complete search history.

(56) References Cited

U.S. PATENT DOCUMENTS

| | | | | |
|---|---|---|---|---|
| 5,089,017 A * | 2/1992 | Young et al. | ................. | 623/3.11 |
| 5,498,228 A * | 3/1996 | Royalty et al. | ................... | 600/16 |
| 6,778,856 B2 * | 8/2004 | Connelly et al. | ................ | 607/32 |
| 7,007,696 B2 | 3/2006 | Palkon et al. | | |
| 2004/0162463 A1* | 8/2004 | Lau et al. | ........................ | 600/37 |
| 2005/0160823 A1* | 7/2005 | Zdeblick et al. | ................ | 73/715 |
| 2006/0052833 A1* | 3/2006 | Legay et al. | .................... | 607/27 |

* cited by examiner

*Primary Examiner* — Nicole F Lavert
(74) *Attorney, Agent, or Firm* — Pillsbury Winthrop Shaw Pittman LLP

(57) ABSTRACT

A method for generating a cardiogram is provided. The method includes contacting an anterior surface of a patient's heart with a magnetic mat. The magnetic mat is constructed and arranged to conform to and move with the heart as the heart contracts and relaxes. The method also includes placing an electromagnetic assembly on the patient's chest. The electromagnetic assembly includes an inductive coil and is in functionally cooperative relation with respect to the mat. The method also includes measuring a current generated in the coil by movement of the magnetic mat due to movement of the heart.

16 Claims, 4 Drawing Sheets

METHOD OF GENERATING A CARDIOGRAM WITH A MAGNET

CROSS-REFERENCE TO RELATED APPLICATIONS

This application claims the benefit of priority from U.S. Provisional Patent Application Ser. Nos. 60/755,413, 60/755,414, 60/755,415, 60/755,416, and 60/755,424, all of which were filed Dec. 31, 2005, the contents of which are incorporated herein by reference in their entireties. The present application is related to U.S. patent application Ser. Nos. 11/648,914 (published as U.S. Patent Application Publication No. 2007-0238914 A1), 11/648,635 (published as U.S. Patent Application Publication No. 2007-0156007 A1), 11/648,636 (published as U.S. Patent Application Publication No. 2007-0156008 A1), and 11/648,908 (published as U.S. Patent Application Publication No. 2007-0250162 A1), all of which were filed on Jan. 3, 2007, and are incorporated herein by reference in their entireties.

BACKGROUND OF THE INVENTION

1. Field of the Invention

The present invention generally relates to a device and method for depicting cardiac position and motion. More specifically, the present invention relates to a device and non-radiographic, non-ultrasound, and non-electrocardiogram method of depicting cardiac position and motion.

2. Description of Related Art

During the aging process, weakened or ineffective cardiac muscles may inhibit the cardiac pumping function from either the right, left, or both ventricles. When the pumping activity of the heart cannot meet the body's demands, systemic shock and subsequent organ dysfunction (such as pulmonary edema and renal failure) can result. Weakened heart muscles can also result in an over distended, dilated myocardium, which can have a detrimental effect on the electrical conduction and overall mechanical performance of the heart.

Advances in medical science have attempted to overcome these problems by replacing an impaired heart via heart transplants, or with devices such as artificial hearts. However, heart transplants are difficult to obtain since there is a limited donor supply. Moreover, artificial hearts have proved not entirely effective in duplicating cardiac contractions, are extremely expensive, and are known to be rejected by the human body.

Therefore, rather than replacing the heart, various arrangements have been proposed to assist right and left ventricular output of the existing impaired heart. For example, a number of arrangements are suggested in U.S. Pat. No. 4,621,617 to Sharma ("the '617 patent). FIG. 1 of the '617 patent proposes an arrangement in which two components are disposed in surrounding relation to the heart and function to compress the heart therebetween to assist ventricular output thereof. The two components are furnished with electromagnetic induction circuitry, numerous pole elements, and are secured to one another by a mechanical hinge. It can be appreciated that the device is quite cumbersome, difficult to implant, and has achieved little if any acceptance. FIG. 4 of the '617 patent illustrates an alternate arrangement in which a compressor element is provided posteriorly to the heart and is movable to compress the heart against the rib cage. This embodiment is somewhat more practical, but nevertheless problematic in a number of respects. For example, no means are provided for evaluating the amount of compressive resistance or intra-cardiac pressure of the heart during compression thereof. As a result, the compressor element may either apply insufficient compressive force to the heart, thereby resulting in ineffective ventricular assist, or apply excessive compressive force, thereby damaging the heart. Additionally, providing a compressor element posteriorly to the heart requires complex surgery in which the entire chest cavity must be opened. Moreover, such placement of the compressor element is largely impractical since the aorta, esophagus and spine are all disposed in close proximity to the posterior portion of the heart and leave little room for insertion of any type of assist device.

U.S. Pat. No. 5,498,228 ("the '228 patent"), which is incorporated herein by reference in its entirety, describes an electromagnetic biventricular device that includes an electromagnetic coil that is placed on the anterior chest. When current is passed through the coil, an electromagnetic field is generated posteriorly though the sternum so that the field interfaces with a magnetic field of a magnetic mat that resides on the anterior aspect of the heart. When like poles of the electromagnetic field and the magnetic mat interface, there is a posterior displacement of the magnetic mat on the heart. This takes place during systole. The '228 patent discloses the use of an EKG to assist with the operation of the device.

Present imaging modalities of the heart, which may use radiography, ultrasound, and/or electrocardiograms, are useful to guide intervention in the treatment of various cardiac diseases. These imaging modalities are anatomic and functional. Understanding cardiac contractility in a real-rime fashion may be useful information in guiding therapy with the devices described above.

BRIEF SUMMARY OF THE INVENTION

It is an aspect of the present invention to provide a real-time two-dimensional assessment of cardiac contractility with specific attention to the ventricles of the heart.

In an embodiment of the invention, a method for generating a cardiogram is provided. The method includes contacting an anterior surface of a patient's heart with a magnetic mat. The magnetic mat is constructed and arranged to conform to and move with the heart as the heart contracts and relaxes. The method also includes placing an electromagnetic assembly on the patient's chest. The electromagnetic assembly includes an inductive coil and is in functionally cooperative relation with respect to the mat. The method further includes measuring a current generated in the coil by movement of the magnetic mat, and plotting the current as a function of time in a graphical format.

In an embodiment of the invention, a method for assisting ventricular output in a human heart by compressing the heart against a vertebral body is provided. The method includes contacting an anterior surface of a patient's heart with a magnetic mat. The magnetic mat is constructed and arranged to conform to and move with the heart as the heart contracts and relaxes. The method also includes placing an electromagnetic assembly on the patient's chest. The electromagnetic assembly includes an inductive coil and is in functionally cooperative relation with respect to the mat. The method further includes measuring a current generated in the coil by movement of the magnetic mat due to movement of the heart, plotting the current as a function of time to create a magnet generated cardiogram, providing a current to the electromagnetic assembly to generate an electromagnetic field with the electromagnetic assembly as a function of the magnet generated cardiogram, and moving the magnetic mat disposed anteriorly to the heart towards the vertebral body so as to force the heart against the vertebral body and thereby compress the heart between the magnetic mat and the vertebral body in response to application of the electromagnetic field to the mat.

In an embodiment of the invention, a cardiac assist device adapted to monitor a human heart is provided. The device includes a magnetic mat adapted for mounting inside a human body adjacent the heart. The mat is constructed and arranged to move with the heart as the heart contracts and relaxes. The device also includes an electromagnetic assembly adapted for mounting on the human body in functionally cooperative relation with respect to the mat. The assembly includes an inductive coil constructed and arranged to generate a current upon movement of the mat. The device further includes a plotter constructed and arranged to create a plot of the generated current as a function of time.

These and other aspects and advantages of the invention will be apparent from the following description, the accompanying drawings, and the appended claims.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE INVENTION

Figure 1:
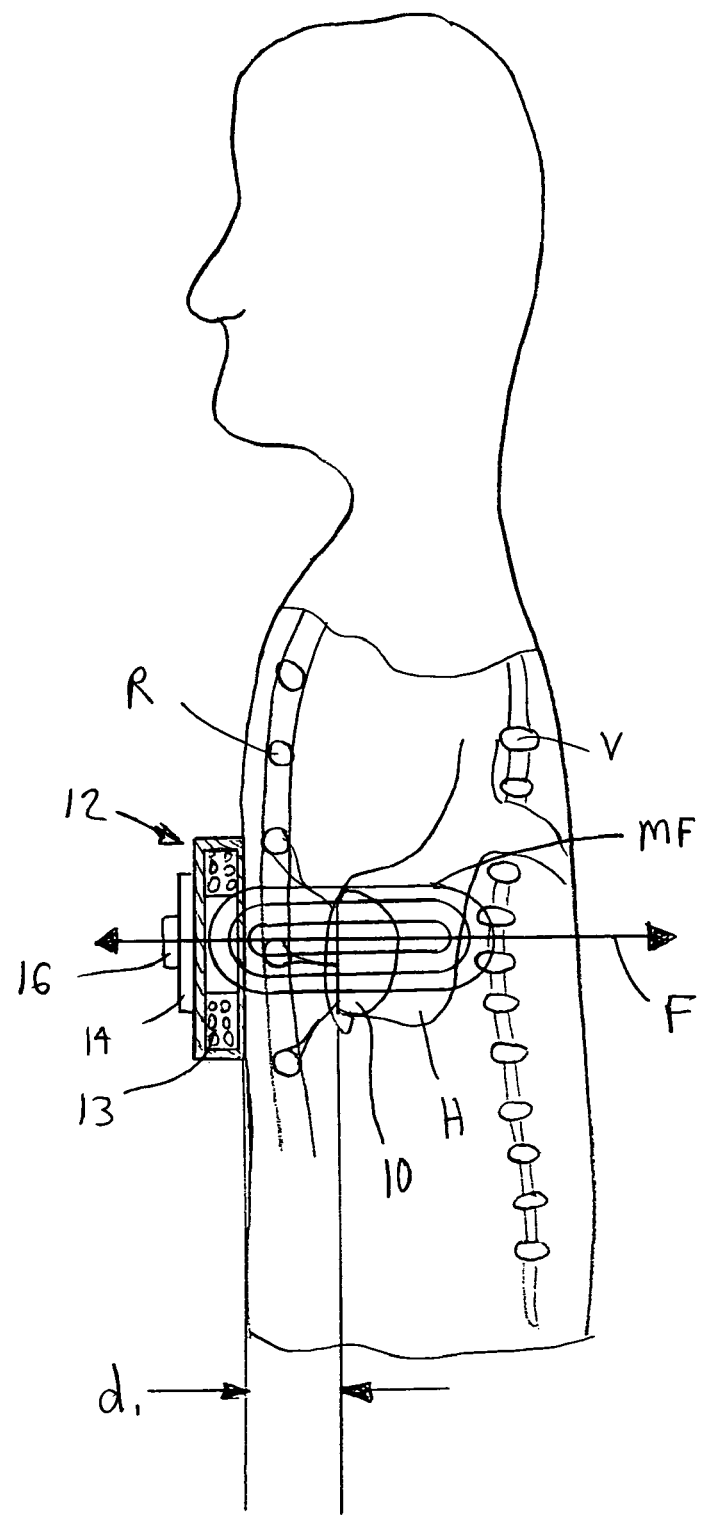
FIG. 1 is a side sectional view of a cardiac assist device according to an embodiment of the present invention shown inside a human body in a neutral relation with the heart.

FIG. 1 is a side sectional view taken through a human body and a cardiac assist, device of an embodiment of the present invention, which is shown in a neutral relation with the human heart. "Neutral relation" as defined herein is a position in which the functioning of the heart is not affected by the cardiac assist device, i.e., the heart is not compressed by the device or expanded by the device, as will be discussed in greater detail below.

In the illustrated embodiment, the device includes a magnetic mat 10 which is adapted to be mounted inside the human body inside of the rib cage R, adjacent the heart H. Preferably, mat 10 is a permanent magnet made from a ferro-magnetic material, including but not limited to samarium cobalt, neodymium iron, and neodymium iron boron (NeFeBo). It can be appreciated, however, that the mat may comprise other materials (such as a superconductive material) so long as the mat is sufficiently responsive to application of an electromagnetic field to compress the heart in accordance with the principles of the present invention. Regardless of the material used, however, the exterior surface of the mat should be chemically inert, and not immunogenic, so that it does not react with blood, tissue, or organs. If necessary, the mat may be coated or surrounded by an inert substance, including but not limited to polyvinyl chloride (PVC), polytetrafluoroethylene (PTFE), or zinc.

The mat 10 is supported within the body, preferably in the space between the anterior aspect of the heart H and the posterior aspect of the pericardium P, although, as will be described later, the mat can also be positioned anteriorly to both the heart and pericardium. Preferably the mat support comprises a plurality of heavy mono-filament threads 20 each having one end secured to the mat and another end secured to the rib cage R (or sternum). The threads are flexible to permit movement of the mat, and should be sufficiently strong to withstand continued flexing without breakage. Where the mat is disposed between the heart and pericardium, the threads 20 are sutured through the pericardium. It can be appreciated that many alternatives to the mono-filament threads can be used to support the mat, as long as such alternatives maintain the mat in movably supported relation, anteriorly and proximate to the heart. As discussed in further detail below, the mat 10 is preferably custom fit to the heart so that is conforms to the heart and is able to move with the heart as the heart beats.

Because the mat 10 is made from a magnetic material, it generates a magnetic field MF. As the heart contracts and expands, the mat 10 moves posteriorly and anteriorly, which also moves the magnetic field MF, as represented by the double arrow line F in FIG. 1.

An electromagnetic assembly 12 is adapted to be mounted externally on the human body, preferably on the chest, in functionally cooperative relation with respect to the mat 10. When the mat 10 is in a neutral relation with the heart, as shown in FIG. 1, the distance between the electromagnetic assembly 12 and an anterior surface of the mat 10 may be represented by $d_1$.

Figure 2:
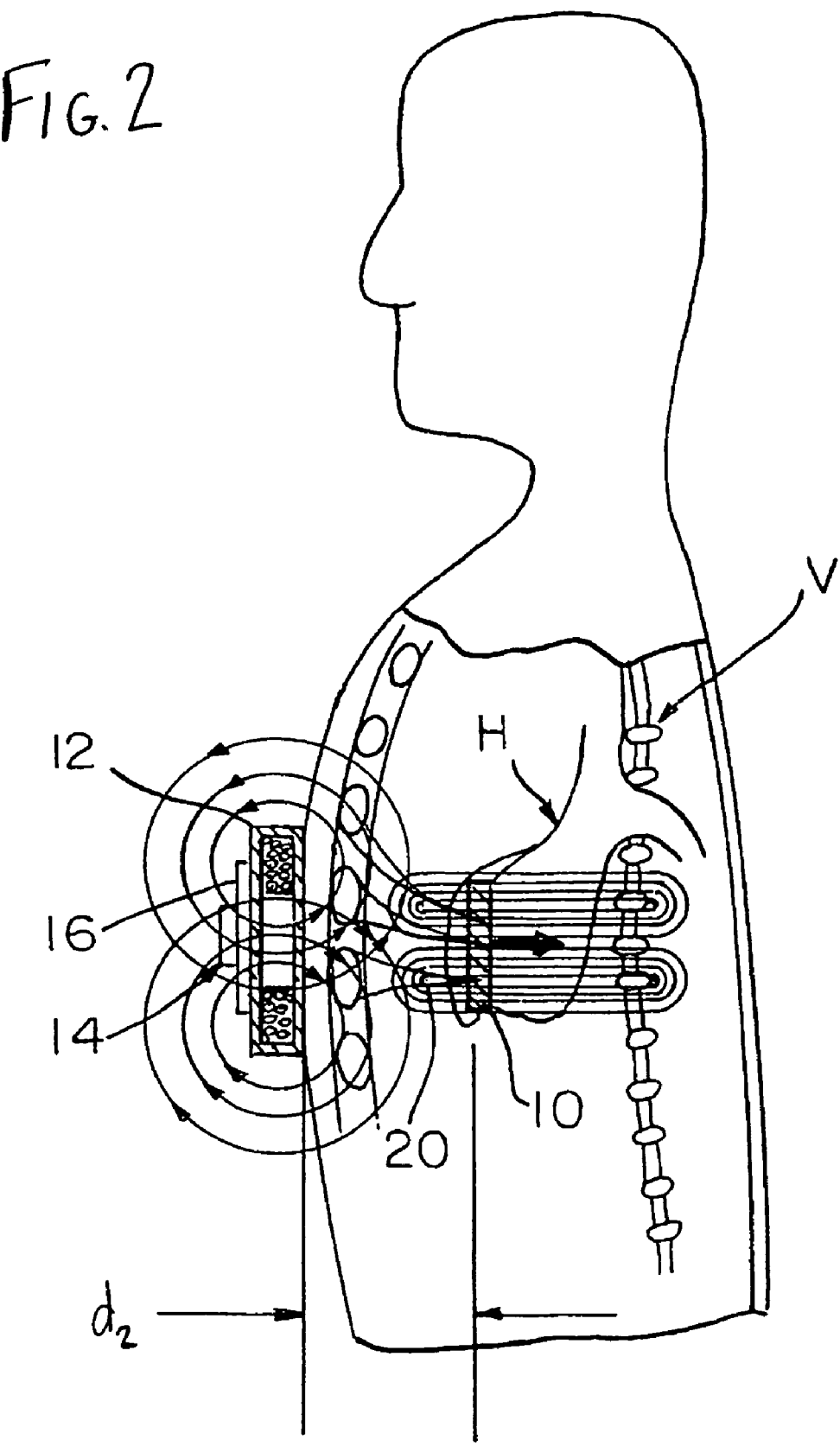
FIG. 2 is a side sectional view of the cardiac assist device of FIG. 1 shown inside the human body in a compressive relation with the heart.
Figure 3:
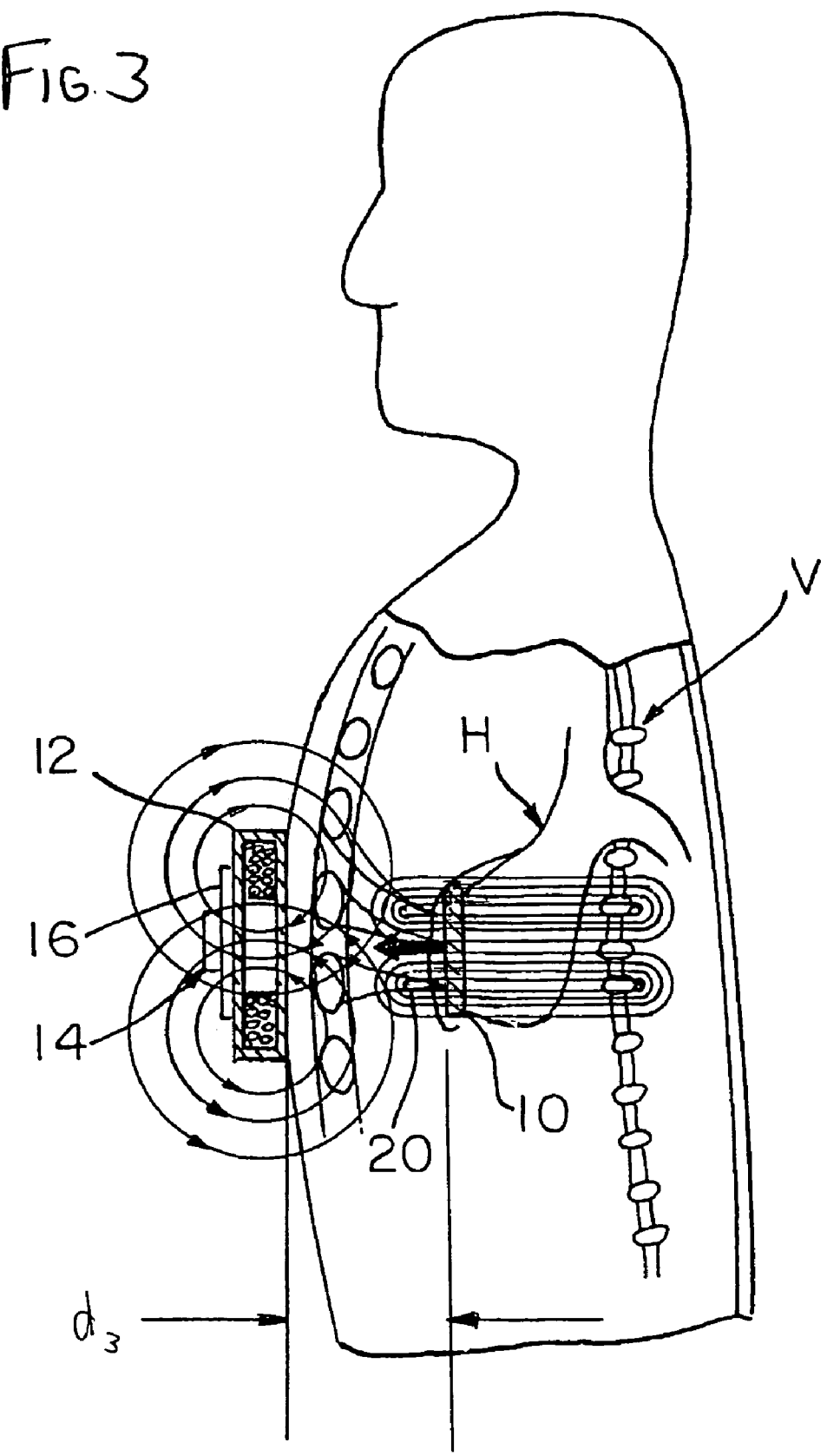
FIG. 3 is a side sectional view of the cardiac assist device of FIG. 1 shown inside the human body in an expansive relation with the heart.

The electromagnetic assembly 12 includes at least one inductive coil 13. When no current is supplied to the coil 13, movement of the mat 10 and the magnetic field MF will generate a small current in the coil 13, as discussed in further detail below. The coil 13 is also configured to be supplied with a current by a power source, preferably a D.C. battery (not shown). When the current is supplied so that it flows in a first direction through the coil 13, it produce a first electromagnetic field, which repels the mat 10 into compressive relation with the heart, as shown in FIG. 2. When the mat 10 is in compressive relation with the heart, the distance between the electromagnetic assembly 12 and an anterior surface of the mat 10 may be represented by $d_2$, which is greater than $d_1$. The power source is also configured to supply a current to the coils 13 in a second direction, which is opposite the first direction, to produce or generate a second electromagnetic field, as shown in FIG. 3. The second electromagnetic field is configured to attract the mat 10 such that the mat is in an expansive relation with, i.e. pulls on, the heart. When the mat 10 is in an expansive relation with the heart, the distance between the electromagnetic assembly 12 and an anterior surface of the mat 10 may be represented by $d_3$, which is less than $d_1$. As the mat 10 moves from the neutral position in a direction that is away from the heart, the heart may expand so as to expand the ventricles in the heart, which may augment the filling of the ventricles.

More particularly, electromagnetic assembly 12 may alternately generate the first and second electromagnetic fields to alternately compress the heart against vertebral body V (e.g., the spine) and expand the heart, thereby assisting the mechanical pumping function of the heart during both systolic and diastolic functions. The magnitude of the force produced by the electromagnetic assembly on the mat will be proportionally dependent on the mat's magnetic field strength, the amount of current traveling through the electromagnetic assembly 12, and the number of current-turns in the electromagnetic assembly 12, but inversely proportional to the distance between the electromagnetic assembly 12 and the mat 10.

Figure 4:
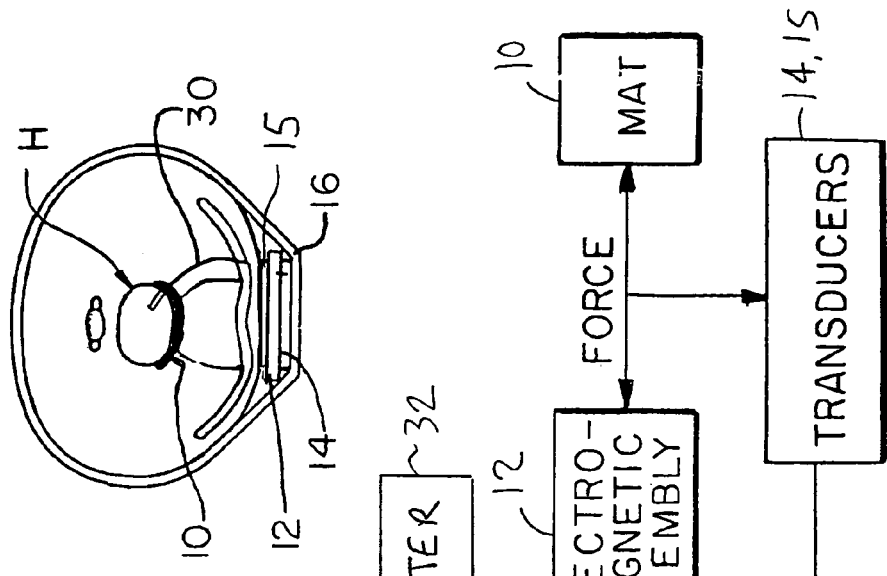
FIG. 4 is a top sectional view of the cardiac assist device of FIG. 1 shown inside the human body.

A first transducer 14 (preferably a load cell, force gauge type, made from piezo AC material) may be secured to the electromagnetic assembly 12 on the side opposite the chest by a preferably rigid harness 16, and a second transducer 15 (again, preferably a load cell, force gauge type, made from piezo AC material), shown in FIG. 4, is secured to the electromagnetic assembly on the same side as the chest. The harness is disposed in surrounding relation to the human torso as shown in FIG. 4, which is a top sectional view through the torso. The harness 16 may include shoulder straps to prevent vertical movement of the electromagnetic assembly 12 when an individual is in the upright position.

Figure 5:
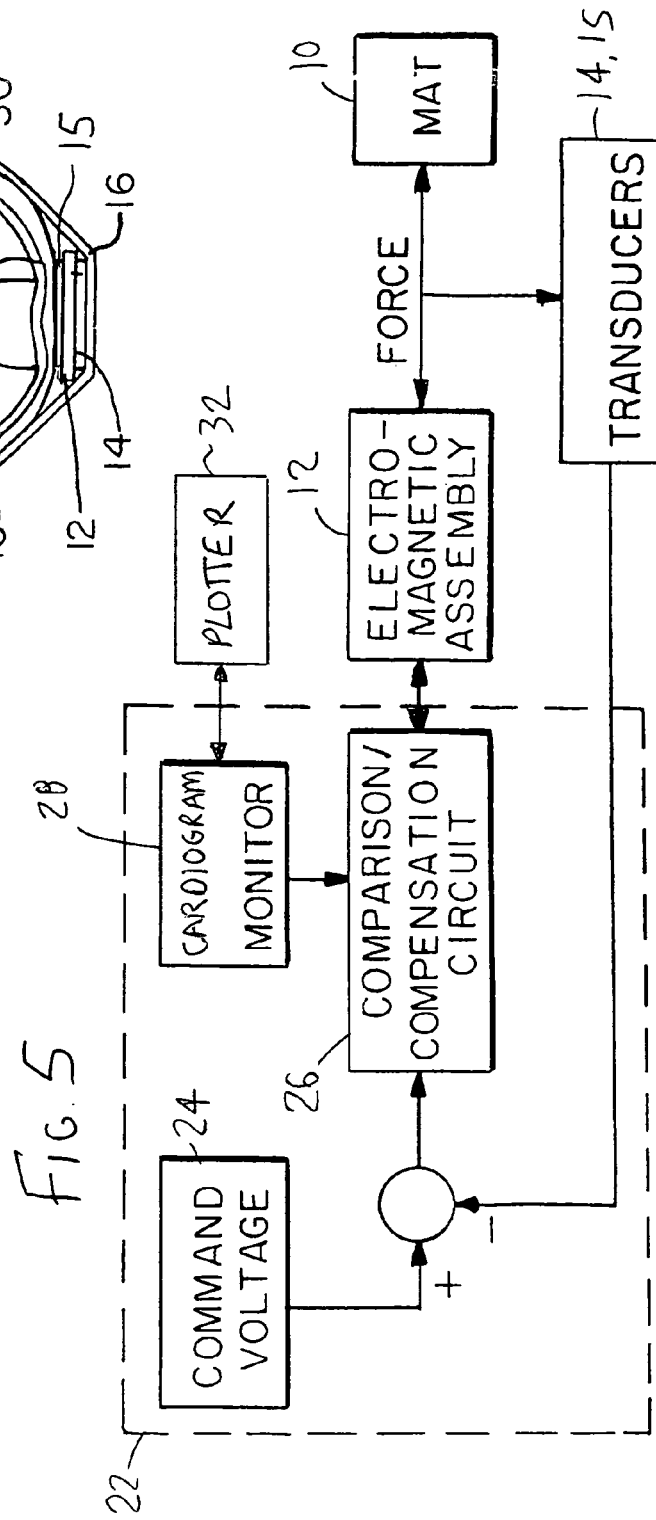
FIG. 5 is a block diagram schematically showing the interrelation of various components of the cardiac assist device of FIG. 1.

As shown in FIG. 5, the transducers 14, 15 form part of an electronic feedback/control loop, and function to evaluate the compressive resistance of the heart during movement of the mat 10 into compressive relation with the heart, and the expansive resistance of the heart during movement of the mat 10 into expansive relation with the heart. More specifically, when the electromagnetic assembly 12 generates the first electromagnetic field to repel the mat 10, an equal and opposite force is applied to the electromagnetic assembly, thus repelling the assembly away from the chest. It can be appreciated that when such an electromagnetic field is generated, the pressure transducer 14 is compressed between the assembly 12 and harness 16 (e.g., see FIG. 2). The transducer 14 senses the compressive pressure or force applied thereto and outputs a voltage proportional to such force or pressure. A control circuit 22 receives the signal generated by the transducer and controls the intensity of the first electromagnetic field generated by the electromagnetic assembly as a function of that signal. As a result, the control circuit effectively controls the degree to which the mat compresses the heart.

Similarly, when the electromagnetic assembly 12 generates the second electromagnetic field to attract the mat 10, an equal force is applied to the electromagnetic assembly 12, thus attracting the assembly toward the chest. It can be appreciated that when such an electromagnetic field is generated, the pressure transducer 15 is compressed between the assembly 12 and the chest. The transducer 15 senses the compressive pressure or force applied thereto and outputs a voltage proportional to such force or pressure. A control circuit 22 receives the signal generated by the transducer and controls the intensity of the second electromagnetic field generated by the electromagnetic assembly as a function of that signal. As a result, the control circuit effectively controls the degree to which the mat expands the heart.

The control circuit 22 includes a compensation/comparison circuit 26 (or "compensation circuit") which compares the voltage generated by the transducers 14, 15 to a command voltage generated by command voltage generator 24. The command voltage corresponds to a predetermined voltage which represents the ideal amount of force required to compress and expand the heart. The compensation/comparison circuit 26 measures the difference between the voltages generated by the pressure transducers 14, 15 and the command voltage, and then digitally compensates for such difference so that an appropriate amount of current is sent through the coils in the electromagnetic assembly 12. For example, if the voltage generated by the respective transducer 14, 15 is less than the command voltage, the compensation circuit 26 will ramp up the current sent through coils 13 and thereby increase the intensity of the magnetic field applied by electromagnetic assembly 12. In contrast, if the voltage generated by the respective transducer 14, 15 is less than the command voltage, the compensation circuit will decrease the amount of current through coils 13 and thereby decrease the intensity of the magnetic field applied by the electromagnetic assembly 12. Thus, the intensity or magnitude of the first and electromagnetic fields generated by the electromagnetic assembly 12 is controlled so that the compressive force applied by the mat 10 to the heart remains within a predetermined range with each compressive stroke, and the tensile force applied by the mat 10 to the heart remains within a predetermined range with each expansive stroke.

The predetermined amount of force to be applied to the heart in order to obtain the desired cardiac output is determined experimentally during an initial procedure wherein a catheter, such as the Swan-Ganz catheter, is placed in the heart to monitor intra-ventricular pressures. This type of catheter is also capable of measuring actual cardiac output. The cardiac output and intra-cardiac pressure are correlated with the voltages generated by the pressure transducers 14, 15, and after several days of experimentation, the Swan-Ganz catheter may be removed. The pressure transducers 14, 15 thereafter generate voltages as a function of the compressive and expansive resistances of the heart, which in turn are a function of either the intra-cardiac pressure or output of the heart.

It can be appreciated that the Swan-Ganz catheter may be kept within the heart and utilized as a transducer in lieu of the transducers 14, 15. Such an arrangement is shown in FIG. 4, wherein a Swan-Ganz catheter 30 is in place. It is advantageous, however, to remove the Swan-Ganz catheter since use thereof requires the provision of wires extending through the human flesh from the catheter to the electromagnetic assembly 12 and control circuit. This may be quite uncomfortable for the subject.

While the magnitude of the first and second electromagnetic fields generated by electromagnetic assembly 12 is controlled by the control circuit 22 together with the pressure transducers 14, 15, it can be appreciated that the frequency of the first and second electromagnetic fields must coincide with the natural contractions and expansions of the heart. This may be accomplished by use of a cardiogram monitor 28 integrated into the control circuit.

In an embodiment, the monitor may be an electrocardiogram (EKG) monitor that measures the electrical activity of the heart and, together with the rest of the control circuit, functions to synchronize the first electromagnetic field generated by the electromagnetic assembly with the QRS spike of the electrocardiogram. This technique of adjusting the rate at which the mat compresses the heart is similar to that used in intra-aortic balloon pumps, and is conventional in this field of technology. The application of the first electromagnetic field may be specifically timed during systole and determined in a custom manner for each patient with regard to the duration of the compression, the change in pressure as a function of change in time in the specific time interval relative to the QRS wave or systolic segment. These three variables may be optimized, as determined by the best cardiac output during the initial phase devise treatment. Alternatively, or in addition to the EKG monitor, the device itself may be used to generate a magnet cardiogram based on the movement of the heart, as discussed in further detail below.

The current supplied to the electromagnet (i.e. coils) of the electromagnetic assembly 12, which sits on the anterior aspect of the chest, may be reversed during diastole in an effort to improve diastolic filling of the ventricles. As discussed above, this results in a polarity switch of the electromagnet and instead of repelling the magnetic mat as previously described and shown in FIG. 2, the magnetic mat is drawn towards the sternum and away from the anterior aspect of the heart, as shown in FIG. 3. Because of the uniform apposition of the anterior aspect of the heart to the posterior aspect of the magnetic mat (which may be further enhanced by the custom manufacture of each magnetic mat per patient, as described in U.S. Provisional Patent Application Ser. No. 60/755,424, which is incorporated herein by reference, and U.S. patent application Ser. No. 11/648,635 (published as U.S. Patent Application Publication No. 2007-0156007 A1), which is incorporated herein by reference), significant suction and negative pressure may take place between the anterior aspect of the heart and the posterior aspect of the magnetic mat. As the ribs of the patient's chest move laterally and superiorly with each inspiration, significant negative pressure may take place between the rib cage and the lung parenchyma. This may result in an expansion of the lung tissue.

In a similar fashion, as the magnetic polarity of the coil is reversed, the magnetic mat is drawn anteriorly, and due to the negative pressure between the magnet in the anterior surface of the heart over the ventricles, the ventricles expand. As the ventricles expand, ventricular filling is augmented, and evacuation of the atrium and atrial emptying may occur. The quicker the pressure in the venous tree can be reduced, and the further the right heart and venous pressure can be reduced, the easier it should be for the arterial blood to perfuse the extremities and deliver oxygen. This may also decrease the risk for hepatic congestion. Although there is significant resistance produced by the venous tree, the resistance may be changed, which may improve the diastolic function of the heart.

As a general rule, when the diastolic function of the heart improves, cardiac output improves. Just as the systolic augmentation (i.e., compression of the heart) is dependent on timing onset, duration, and the pressure curve actuation in improving systolic ejection fraction, diastolic augmentation is dependent on accurate time onset, duration segment, and pressure curve actuation. The signal provided by a cardiogram, such as an EKG, may be used to assist in the timing of the current reversal and generation of the second magnetic field.

The preferred procedure for inserting the mat 10 into the human body in cooperative relation the heart will now be described. The heavy mono-filament threads 20 each have one end thereof secured to the peripheral edges of two opposite sides of the mat, which preferably has a substantially rectangular or oval shape. An incision is made immediately below the breastbone using the sub-xiphoid approach, and the threads are then sutured to the rib cage and/or sternum by use of curved trochar sheath. The sutures are passed anteriorly to the epicardium, but posterior to the anterior aspect of the pericardium, and exit intercostally lateral to the sternum. Enough slack should be left in the mono-filament sutures to permit movement of the mat 10 away from the electromagnetic assembly 12 into compressive relation with the heart upon application of the electromagnetic fields.

In an embodiment of the present invention, the cardiac assist device itself may be configured to create a cardiogram that is independent from the EKG, as well as an image of the position of the heart. In this embodiment, each patient being considered for cardiac assist with the electromagnetic cardiac assist device described above may first undergo a CAT scan of the chest, preferably with 1.5 mm cuts, to allow a three-dimensional model to be made of that particular patient's heart morphology. The magnetic mat 10 may then be constructed for that unique individual heart morphology. Preferably, the mat 10 is made from neodymium iron boron (NeFeBo) having a zinc coating, although other suitable magnetic materials, such as those described above, may be used. During construction, specific attention is given to the posterior aspect of the magnetic mat so that there is uniform conformity of the posterior surface of the magnetic mat and the anterior surface of the heart. This allows the mat to be constructed so that it substantially conforms to the patient's heart once the mat is inserted into the patient, such as in the manner described above, without having to flex the mat 10. Forming the mat so it substantially conforms with the shape of the patient's heart rather than flexing a flexible mat, as described in the '228 patent, reduces the amount of stress in the mat, which may enhance the stability of the mat and allow the mat to be more responsive to the movement of the heart.

Because the magnetic mat is custom fitted to the anterior surface of the heart, the mat will move with each contraction and relaxation of the heart. For example, with diastolic filling of the ventricles, there will be anterior movement of the magnetic mat. With systolic contraction of the ventricles, there will be posterior movement of the magnetic mat. As the magnetic mat 10 moves anteriorly and posteriorly, the lines of force from the magnetic mat 10 will pass through the coil 13 of the electromagnetic assembly 12, as shown in FIG. 1, which will generate a current in the coil 13. That is, if the coil 13 is left "dormant" and does not receive active current from a power source, a current will be generated in the coil 13 as a result of the movement of the lines of force from the magnetic field MF of the mat 10 as it moves with the heart. This current may be translated to a waveform on a time axis. Although the amount of current may be relatively small, it will still be detectable and usable to plot the movement of the heart as a function of time in a graphical format with a plotter 32, shown in FIG. 5. The graphical format may be displayed on a display device, which may be part of the monitor 28. In addition, the information may be used in place of the information provided by the EKG, as described above.

In an embodiment, an array of coils may be used in the electromagnetic assembly 12 as sensors that are configured to more precisely sense the movement of different portions of the heart. This would allow multiple waveforms to be generated, thereby providing indications at different surface areas regarding movement of the heart. For example, different coils may be positioned to target the different ventricles of the heart. This may produce multiple plots, which may be individually analyzed and/or cumulatively analyzed. The magnet cardiogram so generated will give an indication of systole and diastole and an indication of contractility, i.e., whether the contractility is present or is not present. Contractility in regard to systole may be useful for actuating the electromagnetic biventricular assist device described above.

For example, diastolic expansion of the ventricles will produce a different waveform, and such a plot may be useful for timing diastolic decompression with the electromagnetic biventricular assist device. The current provided to the coil 13 is not continuous during the entire cardiac cycle, but instead is discrete, because there is discrete energy delivery during a certain segment of systole, and there is a discrete decompression current reversal during diastole. When the coil is used passively (i.e., no current is provided to the coil with a power source) to reflect systole and diastole, current delivery segments may be applied at intervals that are most optimal to augment cardiac output, as determined by the Swan-Ganz catheter or a noninvasive impedance device. In addition, the current delivery and current reversal for systolic augmentation, as described above, does not need to be delivered every cardiac cycle. In embodiments of the invention, the current delivery and current reversal for systolic augmentation may be delivered every second or third or fourth heart beat. Optimal actuation rate and frequency may be experimentally determined with each patient, and over time, standardization may occur. By using the magnetic mat of the cardiac assist assembly to create a cardiogram and provide cardiac assist to the heart, a more compact device (e.g., one that does not need an EKG monitor) may be assembled.

It will be appreciated that the aspects of this invention have been fully and effectively accomplished. It will be realized, however, that the foregoing preferred specific embodiments have been shown and described for the purpose of this invention and is subject to change without departure from such principles. Therefore, this invention includes all modifications encompassed within a spirit and scope of the following claims.

What is claimed is:

1. A method for generating a cardiogram, the method comprising:
    contacting an anterior surface of a patient's heart with a magnetic mat, the magnetic mat being constructed and arranged to conform to and move with the heart as the heart contracts and relaxes;
    placing an electromagnetic assembly on the patient's chest, the electromagnetic assembly comprising an inductive coil and being in functionally cooperative relation with respect to said mat;
    measuring a current generated in the coil by movement of the magnetic mat due to movement of the heart; and
    plotting the current generated in the coil as a function of time in a graphical format.

2. The method according to claim 1, further comprising custom fitting said mat to the heart.

3. The method according to claim 1, wherein the electromagnetic assembly comprises a plurality of coils, and said measuring comprises measuring a plurality of currents generated in the plurality of coils by movement of the magnetic mat due to movement of the heart.

4. The method according to claim 1, further comprising displaying the graphical format.

5. The method according to claim 1, wherein the inductive coil does not receive current from a power source, and wherein current is only generated in the coil by movement of the magnetic mat due to movement of the heart.

6. The method according to claim 3, wherein the plurality of coils are positioned to sense movement of different portions of the heart, and wherein the plurality of measured currents generated in the plurality of coils provide indications at different surface areas regarding movement of the heart.

7. A method for assisting ventricular output in a human heart by compressing the heart against a vertebral body, the method comprising:
    contacting an anterior surface of a patient's heart with a magnetic mat, the magnetic mat being constructed and arranged to conform to and move with the heart as the heart contracts and relaxes;
    placing an electromagnetic assembly on the patient's chest, the electromagnetic assembly comprising an inductive coil and being in functionally cooperative relation with respect to said mat;
    measuring a current generated in the coil by movement of the magnetic mat due to movement of the heart;
    plotting the current generated in the coil as a function of time to create a magnet generated cardiogram;
    providing a current to the electromagnetic assembly to generate an electromagnetic field with the electromagnetic assembly as a function of said magnet generated cardiogram; and
    moving the magnetic mat disposed anteriorly to the heart towards the vertebral body so as to force the heart against the vertebral body and thereby compress the heart between the magnetic mat and the vertebral body in response to application of said electromagnetic field to said mat.

8. The method according to claim 7, further comprising custom fitting said mat to the heart.

9. The method according to claim 7, wherein the electromagnetic assembly comprises a plurality of coils, and said measuring comprises measuring a plurality of currents generated in the plurality of coils by movement of the magnetic mat due to movement of the heart.

10. The method according to claim 9, further comprising plotting the plurality of currents as a function of time in a graphical format.

11. The method according to claim 7, wherein the inductive coil does not receive current from a power source, and wherein current is only generated in the coil by movement of the magnetic mat due to movement of the heart.

12. The method according to claim 9, wherein the plurality of coils are positioned to sense movement of different portions of the heart, and wherein the plurality of measured currents generated in the plurality of coils provide indications at different surface areas regarding movement of the heart.

13. A cardiac assist device adapted to monitor a human heart, the device comprising:
    a magnetic mat adapted for mounting inside a human body adjacent the heart, said mat being constructed and arranged to move with the heart as the heart contracts and relaxes;
    an electromagnetic assembly adapted for mounting on the human body in functionally cooperative relation with respect to said mat, said assembly comprising an inductive coil constructed and arranged to generate a current upon movement of said mat due to movement of the heart; and
    a plotter constructed and arranged to create a plot of the current generated in the coil as a function of time.

14. The device according to claim 13, further comprising a display device constructed and arranged to display the plot of the generated current as a function of time.

15. The device according to claim 13, wherein the inductive coil does not receive current from a power source, and wherein current is only generated in the coil by movement of the magnetic mat due to movement of the heart.

16. The device according to claim 13, wherein the electromagnetic assembly further comprises a plurality of coils that are positioned to sense movement of different portions of the heart, and wherein a plurality of currents generated in the plurality of coils by movement of the magnetic mat due to movement of the heart provide indications at different surface areas regarding movement of the heart.

* * * * *